United States Patent
Zhang et al.

(10) Patent No.: US 7,318,278 B2
(45) Date of Patent: Jan. 15, 2008

(54) METHOD OF MANUFACTURE OF A HEART VALVE SUPPORT FRAME

(75) Inventors: Xiangyang Zhang, Irvine, CA (US); Melissa Denton, Irvine, CA (US); Sanjay Shrivastava, Mountain View, CA (US); Pranav Desai, Anaheim Hills, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 11/028,878

(22) Filed: Jan. 3, 2005

(65) Prior Publication Data

US 2005/0150775 A1 Jul. 14, 2005

Related U.S. Application Data

(63) Continuation of application No. 10/423,019, filed on Apr. 24, 2003, now Pat. No. 7,137,184, which is a continuation of application No. 10/251,651, filed on Sep. 20, 2002, now abandoned.

(51) Int. Cl.
*B21D 51/16* (2006.01)
*A61F 2/24* (2006.01)

(52) U.S. Cl. .................. 29/890.12; 29/447; 29/458; 623/2.42; 205/711; 205/716; 205/727

(58) Field of Classification Search ............ 29/458, 29/890.12, 447; 623/2.11, 2.42; 205/685, 205/704, 705, 711, 716, 727
See application file for complete search history.

(56) References Cited

U.S. PATENT DOCUMENTS 4,035,849 A    7/1977  Angell et al.
4,082,638 A *  4/1978  Jumer ........................ 204/213
4,148,699 A *  4/1979  Mayer et al. ............... 148/243
4,441,216 A    4/1984  Ionescu et al.

(Continued)

FOREIGN PATENT DOCUMENTS

EP     1 132 058       9/2001

(Continued)

OTHER PUBLICATIONS

Setting Shapes in NiTi, www.sma-inc.com/NiTiShapes.html, 1999.

(Continued)

*Primary Examiner*—Essama Omgba
(74) *Attorney, Agent, or Firm*—Rajiv Yaday; Guy Cumberbatch

(57) ABSTRACT

Methods for forming a support frame for flexible leaflet heart valves from a starting blank include converting a two-dimensional starting blank into the three-dimensional support frame. The material may be superelastic, such as NITINOL, and the method may include bending the 2-D blank into the 3-D form and shape setting it. A merely elastic material such as ELGILOY may be used and plastically deformed in stages, possibly accompanied by annealing, to obtain the 3-D shape. Alternatively, a tubular blank could be formed to define a non-tubular shape, typically conical. A method for calculating the precise 2-D blank shape is also disclosed. A mandrel assembly includes a mandrel and ring elements for pressing the blank against the external surface of the mandrel prior to shape setting.

17 Claims, 9 Drawing Sheets

U.S. PATENT DOCUMENTS

| | | | |
|---|---|---|---|
| 4,501,030 A | | 2/1985 | Lane |
| 4,725,274 A | | 2/1988 | Lane et al. |
| 4,776,933 A | * | 10/1988 | Ruhstorfer et al. ......... 205/672 |
| 4,816,029 A | | 3/1989 | Penny, III et al. |
| 5,163,953 A | | 11/1992 | Vince |
| 5,449,385 A | | 9/1995 | Religa et al. |
| 5,522,885 A | | 6/1996 | Love et al. |
| 5,795,460 A | * | 8/1998 | Al-Jiboory et al. ......... 205/705 |
| 5,855,601 A | | 1/1999 | Bessler et al. |
| 5,895,420 A | | 4/1999 | Mirsch, II et al. |
| 5,907,893 A | | 6/1999 | Zadno-Azizi et al. |
| 5,928,281 A | | 7/1999 | Huynh et al. |
| 6,248,222 B1 | * | 6/2001 | Wang .................... 204/297.09 |
| 6,274,027 B1 | * | 8/2001 | Kiya et al. ................. 205/705 |
| 6,296,662 B1 | | 10/2001 | Caffey |
| 6,328,763 B1 | | 12/2001 | Love et al. |
| 6,348,068 B1 | | 2/2002 | Campbell et al. |
| 6,416,650 B1 | * | 7/2002 | Ho ............................. 205/640 |
| 6,447,664 B1 | * | 9/2002 | Taskovics et al. .......... 205/170 |
| 6,478,819 B2 | | 11/2002 | Moe |
| 6,523,679 B1 | * | 2/2003 | Manchester ................ 198/841 |
| 6,539,984 B2 | | 4/2003 | Lam |
| 6,558,418 B2 | | 5/2003 | Carpentier et al. |
| 6,565,591 B2 | * | 5/2003 | Brady et al. ................ 606/200 |
| 6,635,085 B1 | | 10/2003 | Caffey et al. |
| 6,736,845 B2 | | 5/2004 | Marquez et al. |
| 6,790,230 B2 | | 9/2004 | Beyersdorf et al. |
| 6,835,300 B2 | * | 12/2004 | Zhu et al. ................... 205/676 |
| 6,848,975 B2 | * | 2/2005 | Duquette et al. ............. 451/41 |
| 6,875,231 B2 | | 4/2005 | Anduiza et al. |
| 6,887,256 B2 | * | 5/2005 | Gilson et al. ............... 606/200 |
| 6,918,921 B2 | * | 7/2005 | Brady et al. ................ 606/200 |
| 6,974,474 B2 | * | 12/2005 | Pavcnik et al. ............ 623/1.24 |
| 7,137,184 B2 | * | 11/2006 | Schreck ....................... 29/447 |
| 2001/0039450 A1 | * | 11/2001 | Pavcnik et al. ............ 623/1.24 |
| 2002/0049467 A1 | * | 4/2002 | Gilson et al. ............... 606/200 |
| 2003/0065386 A1 | | 4/2003 | Weadock |
| 2003/0130684 A1 | * | 7/2003 | Brady et al. ................ 606/200 |
| 2003/0130729 A1 | | 7/2003 | Paniagua et al. |
| 2003/0144687 A1 | * | 7/2003 | Brady et al. ................ 606/200 |
| 2003/0144689 A1 | * | 7/2003 | Brady et al. ................ 606/200 |
| 2004/0024443 A1 | * | 2/2004 | Dwyer et al. .............. 623/1.13 |
| 2004/0078950 A1 | * | 4/2004 | Schreck ....................... 29/447 |
| 2004/0093013 A1 | * | 5/2004 | Brady et al. ................ 606/200 |
| 2004/0117001 A1 | * | 6/2004 | Pelton et al. .............. 623/1.15 |
| 2004/0127934 A1 | * | 7/2004 | Gilson et al. ............... 606/200 |
| 2004/0186558 A1 | * | 9/2004 | Pavcnik et al. ............ 623/1.24 |
| 2004/0186563 A1 | | 9/2004 | Lobbi |
| 2005/0234502 A1 | * | 10/2005 | Gilson et al. ............... 606/200 |

FOREIGN PATENT DOCUMENTS

| | | |
|---|---|---|
| GB | 2056 023 | 3/1981 |
| JP | 63030136 A | 2/1988 |
| WO | WO 00/42950 | 7/2000 |
| WO | WO 00/47139 | 8/2000 |

OTHER PUBLICATIONS

Biocompatibility of NiTi, www.sma-inc.com/biocomp.html, 1999.

* cited by examiner

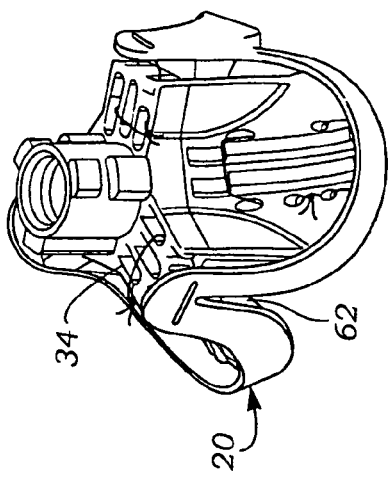
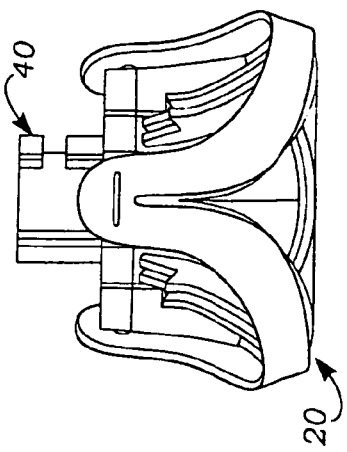
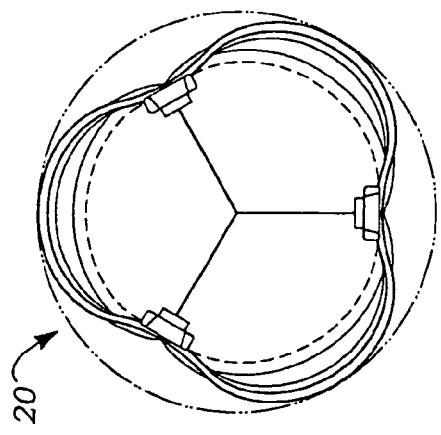
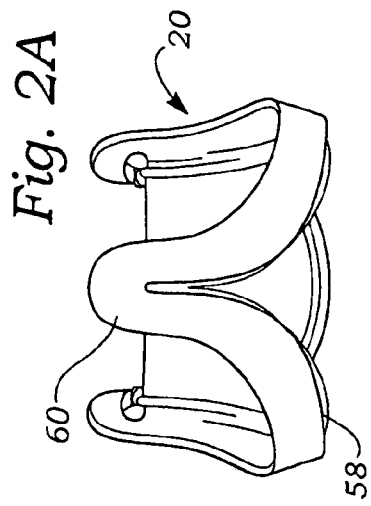
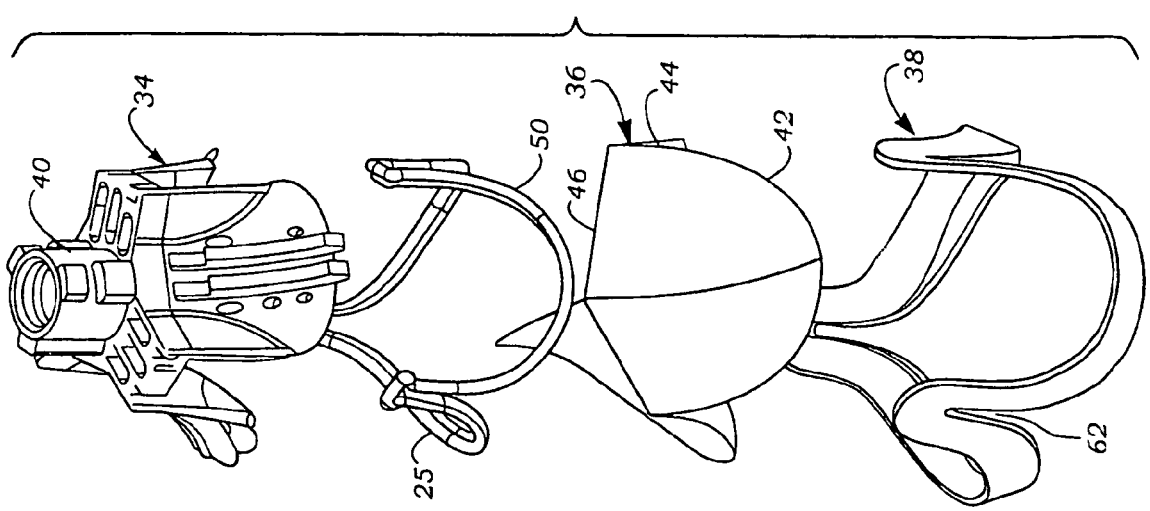

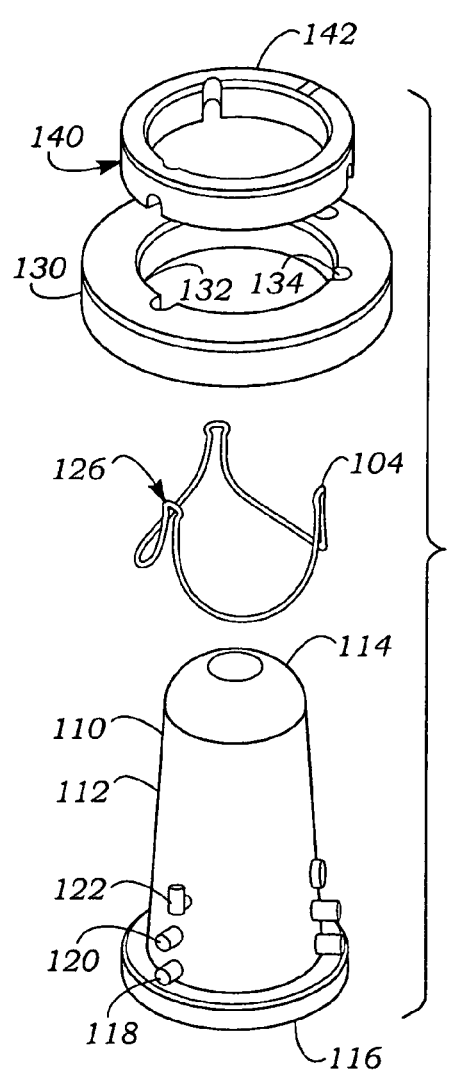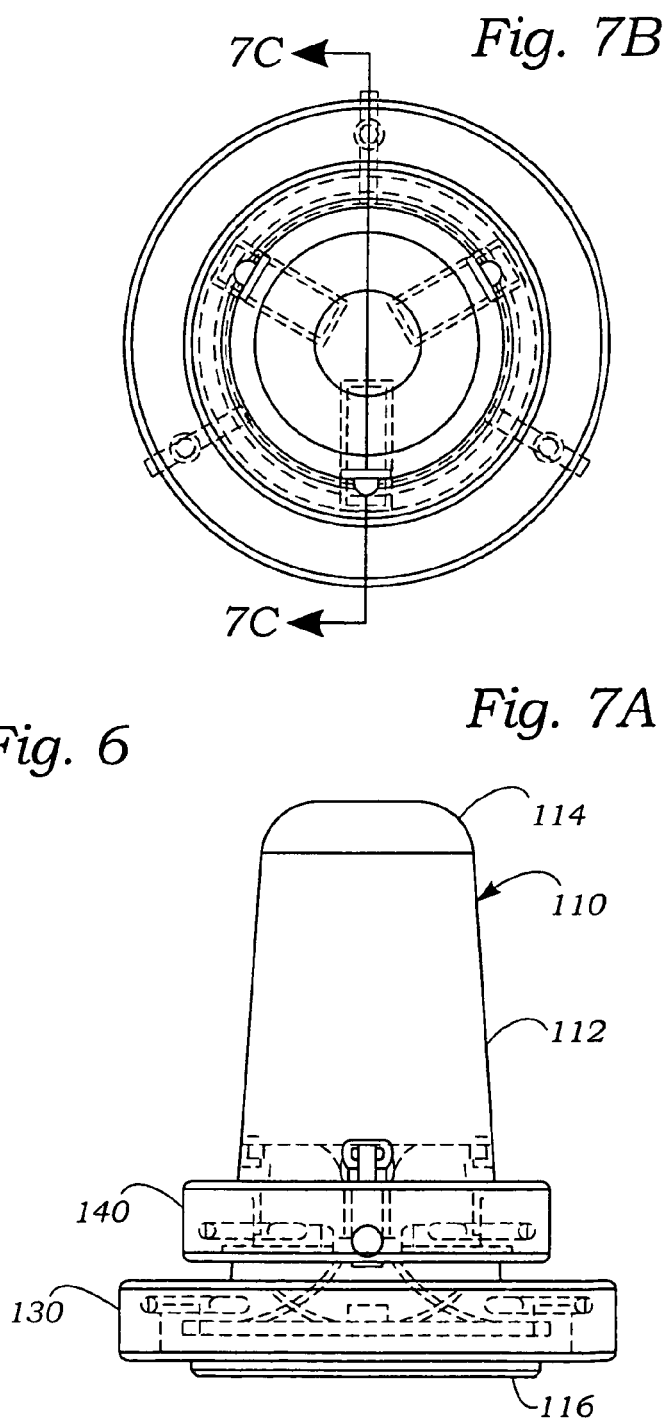

METHOD OF MANUFACTURE OF A HEART VALVE SUPPORT FRAME

RELATED APPLICATIONS

The present application is a continuation of U.S. application Ser. No. 10/423,019, filed Apr. 24, 2003, now U.S. Pat No. 7,137,184 which is a continuation of U.S. application Ser. No. 10/251,651, filed on Sep. 20, 2002, now abandoned

FIELD OF THE INVENTION

The present invention relates generally to medical devices, and more particularly to a continuous three-dimensional support frame for use in heart valves, and methods and apparatuses for forming such support frames.

BACKGROUND OF THE INVENTION

Two primary types of heart valve replacements or prostheses are known. One is a mechanical-type heart valve that uses a ball and cage arrangement or a pivoting mechanical closure to provide unidirectional blood flow. The other is a tissue-type or "bioprosthetic" valve which is constructed with natural tissue leaflets which function much like those in a natural human heart valve; that is, the leaflets imitate the natural action of the flexible leaflets that form commissures to seal against each other and ensure the one-way blood flow. In tissue valves, a whole xenograft valve (e.g., porcine) or a plurality of xenograft leaflets (e.g., bovine pericardium) provide the tissue leaflet occluding surfaces that are mounted within a surrounding stent structure. Some attempts have been made to simulate such flexible leaflets with polymers and the like, and these designs can be grouped with bioprosthetic valves for the purpose of the present invention.

In most bioprosthetic-type valves, metallic or polymeric structure provides base support for the flexible leaflets, which extend therefrom. One such support is an elastic "support frame," sometimes called a "wireform" or "stent," which has a plurality (typically three) of large radius cusps supporting the cusp region of the leaflets of the bioprosthetic tissue (i.e., either a whole valve or three separate leaflets). The free ends of each two adjacent cusps converge somewhat asymptotically to form upstanding commissures that terminate in tips, each being curved in the opposite direction as the cusps, and having a relatively smaller radius. The support frame typically describes a conical tube with the commissure tips at the small diameter end. This provides an undulating reference shape to which a fixed edge of each leaflet attaches (via components such as fabric and sutures) much like the natural fibrous skeleton in the aortic annulus.

The support frame is typically a non-ferromagnetic metal such as ELGILOY (a Co—Cr alloy) that possesses substantial elasticity. A common method of forming metallic support frames is to bend a wire into a flat (two-dimensional) undulating pattern of the alternating cusps and commissures, and then roll the flat pattern into a tube using a cylindrical roller. The free ends of the resulting three-dimensional shape, typically in the asymptotic region of the cusps, are then fastened together using a tubular splice that is plastically crimped around the ends. See FIGS. 3 and 4 of U.S. Pat. No. 6,296,662 for a support frame that is crimped together at a cusp midpoint. The plastic deformation of the splice and wire ends therewithin may cause high residual stresses, which can promote fatigue fracture of the support frame, thus reducing the overall life of the heart valve.

Further, the added diameter of the splice may create an unsightly bulge at one location around the valve circumference that may interfere with the implant process or provide a point of stress concentration.

Some valves include polymeric "support frames" rather than metallic, for various reasons. For example, U.S. Pat. No. 5,895,420 discloses a plastic support frame that degrades in the body over time. Despite some favorable attributes of polymeric support frames, for example the ability to mold the complex support frame shape, conventional metallic support frames are generally preferred for their elastic properties, and have a proven track record in highly successfully heart valves. For example, the CARPENTIER-EDWARDS Porcine Heart Valve and PERIMOUNT Pericardial Heart Valve available from Edwards Lifesciences LLC both have ELGILOY support frames and have together enjoyed the leading worldwide market position since 1976.

What is needed then is an improved three-dimensional heart valve support frame without the drawbacks of a conventional spliced support frame. Also needed is a simple and accurate method of manufacturing such a support frame.

SUMMARY OF THE INVENTION

The present invention solves a number of drawbacks associated with conventional spliced support frames or wireforms in that a continuous, seamless length of material eliminates any non-uniformity in the periphery of the frame. The material may be superelastic such that it provides a highly flexible valve that can move with the dynamic pulsations of the surrounding cardiac tissue. In one particularly useful embodiment, the valve is constructed so that it is implanted up the ascending aorta and can expand and contract therewith. The present invention also provides several novel methods of forming support frames.

One such method of the present invention of forming an elastic material into a heart valve support frame includes providing a two-dimensional blank of a continuous support frame in the elastic material, and forming the two-dimensional blank into a continuous three-dimensional heart valve support frame. A flat sheet of the elastic material may be used and the two-dimensional blank separated therefrom, such as by cutting the elastic material along the perimeter of the two-dimensional blank. The elastic material may be a superelastic material. For example, the superelastic material is NITINOL and the step of forming includes heat-setting the NITINOL into the three-dimensional heart valve support frame. Alternatively, the elastic material may be a conventional metal and the step of forming includes plastically deforming and then annealing the metal.

The three-dimensional heart valve support frame may be formed by providing a mandrel and conforming the two-dimensional blank over the mandrel so that it assumes a three-dimensional shape matching the exterior shape of the mandrel. Once the blank is in the desired shape, the properties of the elastic material are altered while on the mandrel such that when it is removed from the mandrel it remains substantially in the three-dimensional shape corresponding to the heart valve support frame. In one embodiment the heart valve support frame includes three cusps and three commissures and the two-dimensional blank accordingly has three cusp regions and three commissure regions. The step of conforming the two-dimensional blank over the mandrel therefore includes orienting the two-dimensional blank over the mandrel by registering the cusp regions and commissure regions with a series of pins provided on the mandrel, and pressing the two-dimensional blank flat against the exterior shape of the mandrel using at least one ring element.

The method may also include surface treating the three-dimensional heart valve support frame to reduce features of high stress concentration. The surface treating can be by mechanical, chemical or electrochemical process, such as electropolishing A further aspect of the present invention is a method of calculating the shape of and making a heart valve support frame, comprising:

entering the desired shape of a heart valve support frame into a finite element program to obtain a three-dimensional support frame model;

simulating forces on the support frame model to cause it to assume a two-dimensional pattern; and using the shape of the two-dimensional pattern to form a two-dimensional blank from a sheet of elastic material.

The method desirably includes forming the two-dimensional blank into a three-dimensional heart valve support frame by providing a mandrel and conforming the two-dimensional blank over the mandrel so that it assumes a three-dimensional shape matching the exterior shape of the mandrel. If the elastic material is a superelastic material the method may include altering the material properties of the blank while on the mandrel such that when it is removed from the mandrel it remains substantially in the three-dimensional shape of the mandrel. The support frame model may define three arcuate cusps separated by three generally axially oriented commissures, wherein the step of simulating forces involves simulating the application of generally axially oriented forces on the model such that the commissures rotate inward and the two-dimensional pattern appears substantially like a three-leaf clover.

Prior to forming the two-dimensional blank, the two-dimensional pattern may be formed into a three-dimensional virtual support frame shape within the finite element program and then compared with the desired shape of the heart valve support frame. If the virtual support frame shape does not match the desired shape of the heart valve support frame the two-dimensional pattern is adjusted.

Another aspect of the invention is a method of manufacturing a heart valve, including providing a heart valve support frame blank made of superelastic material and forcing the support frame blank into substantially the final shape of a heart valve support frame. While maintaining the support frame blank in its substantially heart valve support frame shape the internal structure of the superelastic material is altered so that it assumes that shape and forms the support frame. Finally, the heart valve is assembled by coupling a bioprosthetic valve or flexible leaflets to the support frame.

The method of manufacture may include providing a tube of the superelastic material. In this configuration, the heart valve support frame blank is provided by separating a continuous support frame blank from the tube. The support frame blank is forced from its tubular configuration to other than a tubular configuration, such as conical, and then the internal structure of the superelastic material is altered. If the material is NITINOL the step of altering includes heat setting the NITINOL.

Alternatively, the method of manufacture may include providing a flat sheet of the superelastic material. In that configuration, the heart valve support frame blank is provided by separating a two-dimensional blank of a continuous support frame from the flat sheet. The two-dimensional blank is forced over a mandrel so that it assumes a three-dimensional shape matching the exterior shape of the mandrel.

Still further, the step of a slender wire of the superelastic material may be provided and bent over a mandrel so that it assumes a three-dimensional shape matching the exterior shape of the mandrel.

One further aspect of the invention is an intermediate apparatus in the formation of a prosthetic tissue-type heart valve comprising a two-dimensional continuous (meaning seamless) heart valve support frame blank. The support frame blank is preferably NITINOL, and may have a square cross-section. The tissue-type heart valve may be of the type having three leaflets, wherein the two-dimensional continuous support frame blank includes three arcuate cusps and three commissures therebetween in a pattern that resembles a three-leaf clover. The commissures each may have widened tips to increase their radius of curvature relative to commissures tips that have not been widened.

A still further aspect of the invention is a method of forming a heart valve support frame, comprising providing a heart valve support frame and electropolishing the heart valve support frame. The heart valve support frame is desirably metallic and has a rectilinear cross-section. More preferably, the heart valve support frame is made of NITINOL. The method may further include, prior to electropolishing, first removing oxidation from the outer surface of the heart valve support frame. One way to removing oxidation is to microblast the outer surface of the heart valve support frame.

The step of electropolishing desirably involves submerging the heart valve support frame into a conductive fluid bath, providing an anode and a cathode, and flowing a current between the anode and the cathode. Plate anodes may be positioned within the conductive fluid bath around the heart valve support frame. The conductive fluid bath preferably comprises nitric acid and methanol maintained at a temperature of between about −28-32° C. In an exemplary embodiment, the conductive fluid bath is maintained at a conductivity level of between about 140-190 µs at 23° C. and the current flows at a voltage of between about 9-10 V.

The heart valve support frame may have an undulating shape with three cusps and three commissures and the method further includes within the conductive fluid bath, holding the heart valve support frame at three points around the undulating shape, and periodically repositioning the heart valve support frame during the electropolishing process. For example, the heart valve support frame may be rotated 120° twice from an initial position.

BRIEF DESCRIPTION OF THE DRAWINGS

FIGS. 2A and 2B are elevational and top plan views, respectively, of an assembled prosthetic heart valve of the present invention;

FIG. 2C is an exploded perspective view of the components of the heart valve of the present invention along with an implantation holder;

FIGS. 2D and 2E are perspective and elevational views, respectively, of the implantation holder attached to the prosthetic heart valve;

FIG. 6 is an exploded perspective view of a heart valve support frame and mandrel apparatus for forming thereof;

FIGS. 7A and 7B are elevational and plan views, respectively of the assembled mandrel apparatus and heart valve support frame;

DESCRIPTION OF THE PREFERRED EMBODIMENTS

The present invention provides an improved support frame, forming apparatus, and method as described herein and shown in the accompanying drawings.

The present invention pertains primarily to flexible leaflet heart valve support frames, which are also referred to in the art as stents or wireforms. As mentioned above, the flexible leaflets can be provided by a biological (i.e., xenograft) valve, biological leaflets, or synthetic leaflets. In this context, a "support frame" for a flexible leaflet heart valve provides the primary internal structural support for the leaflets, and substantially mimics the natural fibrous skeleton of the respective valve annulus. More specifically, each of the leaflets has an outer edge that is coupled to a portion of the support frame such that its inner edge is free to move within the orifice area of the valve, thus providing the opening and closing surfaces thereof. In the common three-leaflet prosthetic valves, the support frame has an undulating shape with three arcuate cusps on the inflow end separated by three upstanding and generally axially-oriented commissures on the outflow end. Around the circumference of the frame, the shape has an alternating structure of cusp-commissure-cusp-commissure-cusp-commissure, and generally describes a tubular surface of revolution about an axis. Some support frames describe a conical surface of revolution with the three commissures on the outflow end of the valve being closer together than the three cusps. It should be understood, however, that the present invention is not limited to support frames for three-leaflet valves, and valves with two or more than three leaflets may be constructed using the support frames embodied herein.

Figure 1:
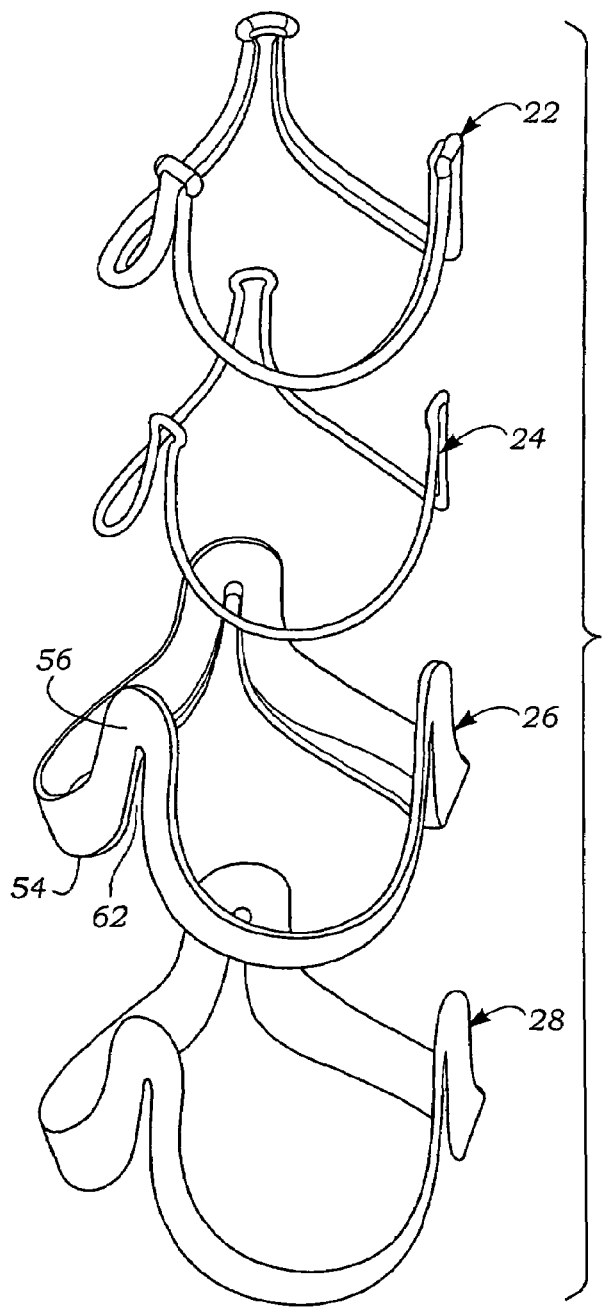
FIG. 1 is an exploded perspective view illustrating subassemblies of a prosthetic heart valve of the present invention.

With reference now to FIG. 1, an exploded view of a number of components of an exemplary embodiment of a prosthetic heart valve 20 (shown assembled FIGS. 2A and 2B) of the present invention is shown. For purposes of discussion, the directions up and down, upper and lower, or top and bottom, are used with reference to FIG. 1, but of course the valve can be oriented in any direction both prior to and after implantation. From top to bottom, the heart valve 20 comprises a fabric support frame covering 22, a support frame 24, an implantation band 26, and a fabric covering 28 for the implantation band. Each of the components seen in FIG. 1 is procured and assembled separately and then joined with the other subassemblies to form the fully assembled valve 20 seen in FIG. 2A.

Figure 1A:
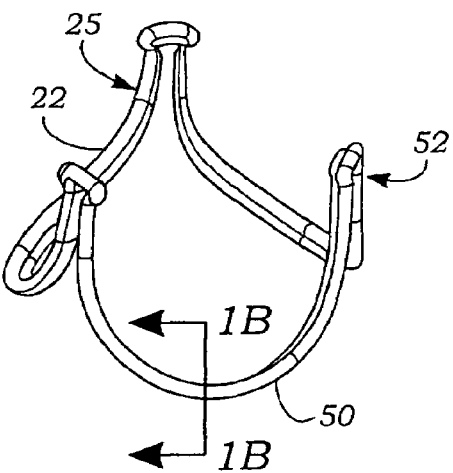
FIG. 1A is a perspective view of a cloth-cover heart valve support frame of the present invention.
Figure 1B:
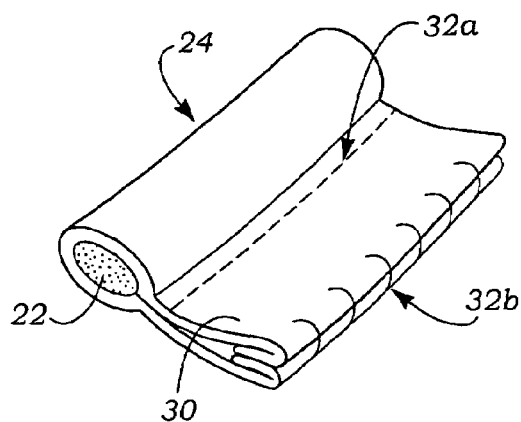
FIG. 1B is a sectional view through the support frame of FIG. 1A, taken along line 1B-1B.

FIG. 1A illustrates a subassembly 25 of the support frame 24 and fabric covering 22 thereover. The cross-section of FIG. 1B more clearly shows the construction of the subassembly. For purpose of attaching to the remaining components, a flat or flange 30 is formed by additional fabric material that has been sewn in two places 32a, 32b as shown.

FIG. 2C is an exploded view of the components of heart valve 20, in addition to an implantation holder 34. The support frame/fabric covering subassembly 25 is shown above a group of three flexible leaflets 36, which, in turn, is above a subassembly 38 comprising the implantation band 26 and its fabric covering 28. These three subassemblies are attached together, such as by sewing, to result in the assembled valve 20 as seen in FIGS. 2A and 2B. Finally, FIGS. 2D and 2E show the holder 34 mounted on the valve 20. Although not shown, an elongated handle can be attached to a threaded boss 40 on the holder for manipulating the valve into its implant position.

Each of the components or subassemblies seen in FIGS. 1 and 2 include three cusps separated by three commissures. For example, each of the leaflets 36 includes an arcuate lower cusp edge 42 terminating in upstanding commissure regions 44. Each leaflet 36 includes a coapting or free edge 46 opposite the cusp edge 42. In the assembled valve 20, the cusp edges 42 and commissure regions 44 are secured around the periphery of the valve, with the free edges 46 permitted to meet or "coapt" in the middle. The support frame subassembly 25 also includes three cusps 50 separated by three upstanding commissures 52. In like manner, the implantation band 26 includes three cusp portions 54 separated by three upstanding commissure portions 56. As seen in FIG. 2A, the assembled valve 20 exhibits cusps 58 and commissures 60.

Further details of the sub-assemblies can be found in U.S. Pat. No. 6,558,418, entitled FLEXIBLE HEART VALVE, filed on Jun. 14, 1999, which disclosure is expressly incorporated herein by reference. As described in this earlier application, the implantation band subassembly 38 is sewn or otherwise attached to the exterior of a further subassembly comprising the group of leaflets 36 attached to the support frame subassembly 25. Outer margins of the implantation band subassembly 38 extend outward from the rest of the valve and provide a platform through which sutures can pass to attach the valve 20 to the patient's anatomy.

The heart valve 20 illustrated is designed to be attached not only at the aortic annulus, but also up into the ascending aorta. The commissure portions 56 of the implantation band 26 are separated about a gap 62 (see FIG. 1) extending substantially all the way up. Likewise, the support frame subassembly 25 is highly flexible such that the cusps 50 generally pivot about the outstanding commissures 52. Ultimately, the cusps 58 of the valve 20, are surgically attached adjacent the patient's annulus, while the upstanding commissures 60 are attached along the ascending aorta. The high flexibility of the valve 20 permits relative movement between these anatomical locations.

In an exemplary embodiment of the present invention, the internal support frame 22 of the subassembly 25 is made of a material that is highly flexible so as to permit maximum relative movement between the valve cusps 58 and commissures 60. That said, the support frame 22 must possess a minimum amount of stiffness to provide the desired support to the leaflets 36. Therefore, there is a balance obtained between the requisite flexibility and stiffness.

The material for the internal support frame is desirably "elastic," which means that it has a relatively high modulus of elasticity, preferably greater than or equal to 26 Msi. Polymers are generally excluded from this definition, although it is conceivable that special formulations might function under these requirements. Various NITINOL alloys can also be suitable for making the internal support frame of the present invention as in certain circumstances they are considered to be "superelastic." Other materials that maybe used include ELGILOY, titanium, stainless-steel, and similar expedients. These latter materials do not display superelasticity but are still elastic. Other materials may fit within this definition but they must be suitable for long-term implantation in the body.

The term "superelastic" (sometimes "pseudoelastic") refers to that property of some materials to undergo extreme strains (up to 8%) without reaching their failure stress limit. Some so-called shape memory alloys (SMAs) are known to display a superelastic phenomena or rubber-like behavior in which a strain attained beyond the elastic limit of the SMA material during loading is recovered during unloading. This superelastic phenomenon occurs when load is applied to an austenitic SMA article which first deforms elastically up to the yield point of the SMA material (sometimes referred to as the critical stress). Upon the further imposition of load, the SMA material begins to transform into stress-induced martensite or "SIM." This transformation takes place at essentially constant stress, up to the point where the SMA material is completely transformed into martensite. When the stress is removed, the SMA material will revert back into austenite and the article will return to its original, pre-programmed programmed or memorized shape.

Figure 3:
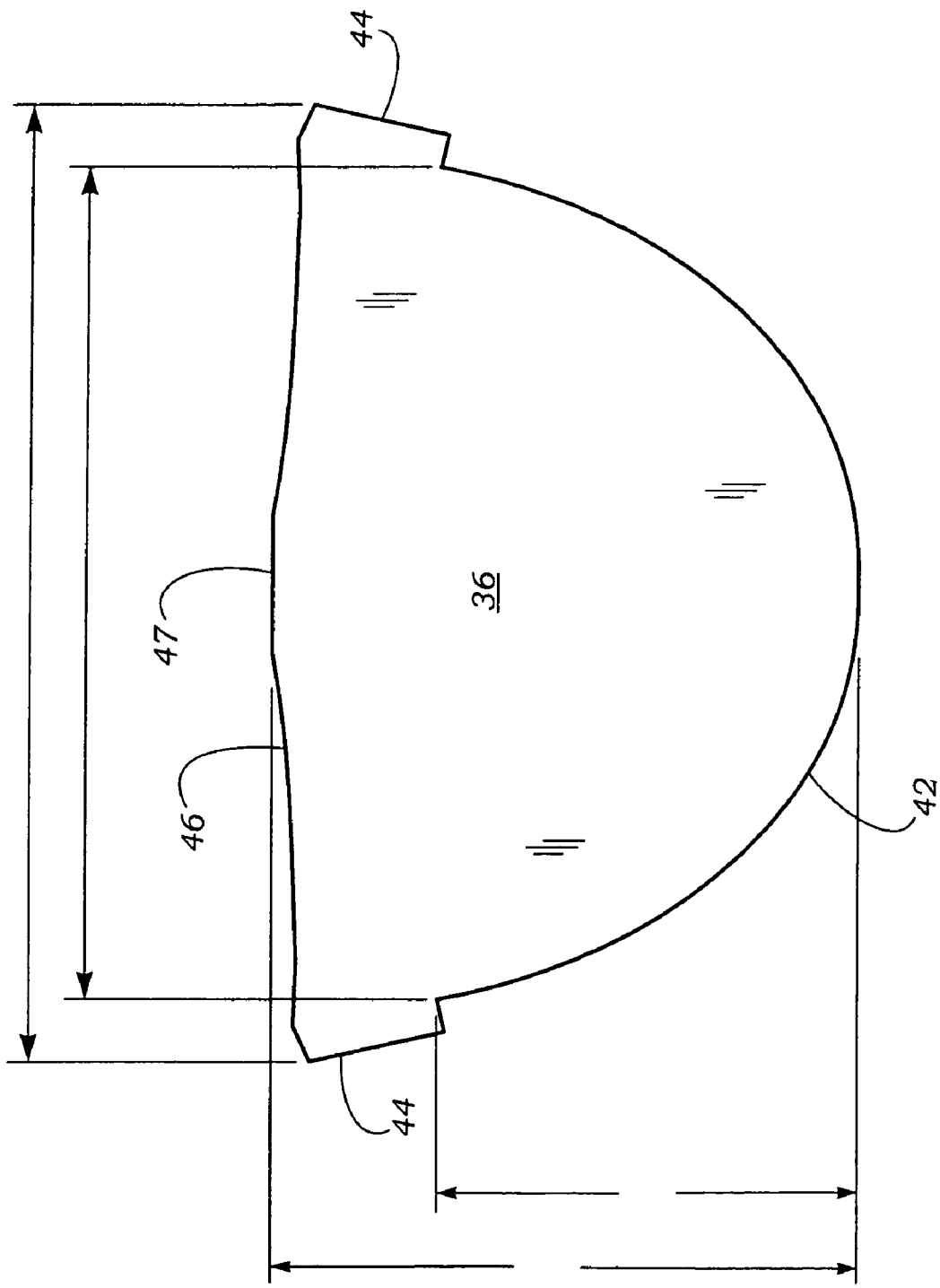
FIG. 3 is a plan view of one flexible leaflet suitable for use in the heart valve of FIG. 2A.

FIG. 3 illustrates one of the leaflets 36 in plan view. As mentioned, the leaflet 36 has an arcuate cusp edge 42 a pair of commissure regions 44, and a free edge 46. The free edge 46 can be non-linear; e.g., the free edge in FIG. 3 increases to a flat portion 47 in the center thereof.

Figure 4A:
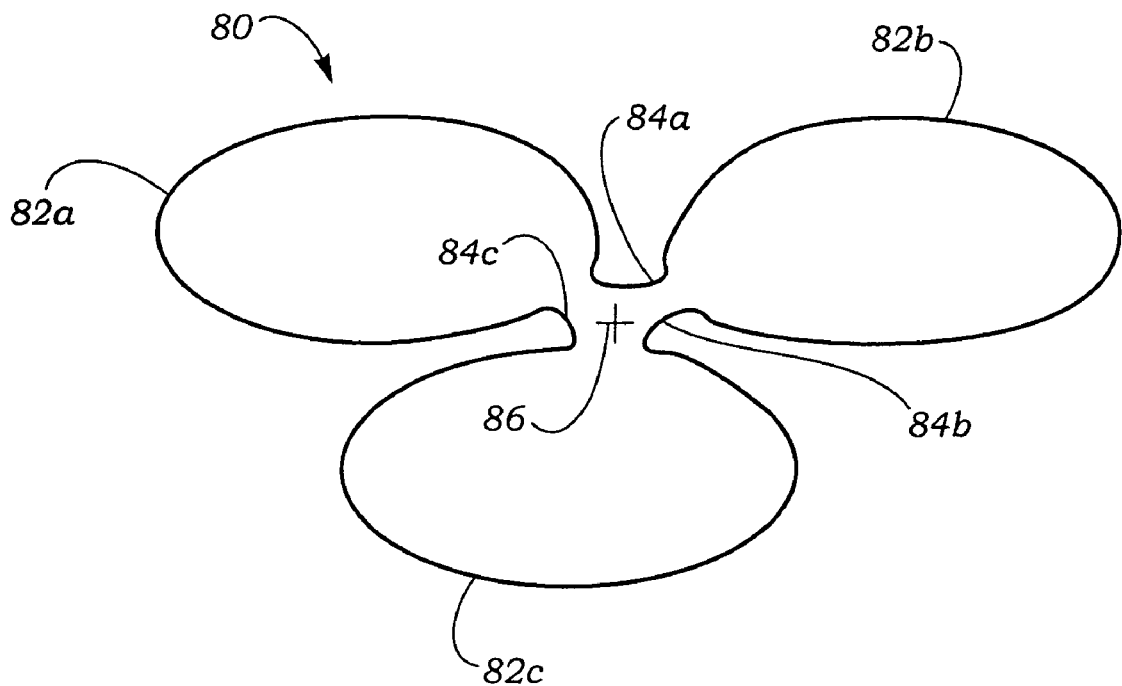
FIG. 4A is a schematic perspective line drawing of a two-dimensional pattern of a heart valve support frame representing an intermediate product in the support frame manufacturing process.
Figure 4B:
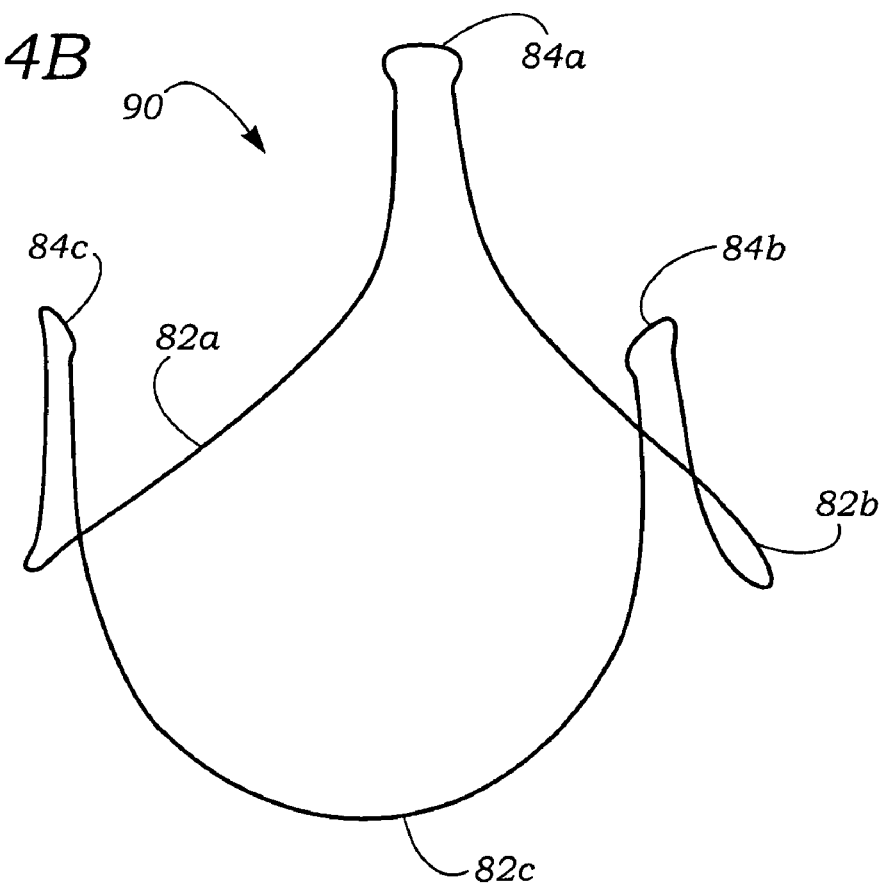
FIG. 4B is a schematic perspective line drawing of a three-dimensional pattern of the heart valve support frame formed from the two-dimensional pattern of FIG. 4A.

FIGS. 4A and 4B are schematic perspective line drawings of stages in the manufacturing process of a heart valve support frame of the present invention. FIG. 4A illustrates a two-dimensional pattern 80 of the support frame representing an intermediate apparatus in the manufacturing process. When viewed from above, the pattern 80 resembles a three-leaf clover with three outwardly extending generally circular lobes or cusps 82a, 82b, 82c separated by three inwardly directed commissures 84a, 84b, 84c. The cusps 82 and commissures 84 are evenly distributed 120° apart about a central axis 86. FIG. 4B is a three-dimensional pattern 90 of the support frame that is made by starting with the two-dimensional pattern 80. Generally, the commissures 84 have been rotated upward and outward from their position in the pattern 80 of FIG. 4A to their position in the pattern 90 of FIG. 4B. The resulting three-dimensional pattern 90 has the undulating shape described above for heart valve support frames in that the cusps 82 extend in one direction along axis 86 while the commissures 84 extend in the opposite direction. Furthermore, the pattern 90 desirably describes a conical surface of revolution. Of particular note is that the pattern 90 includes no seam or splice that might otherwise provide a stress concentration point in the finished support frame.

Figure 5:
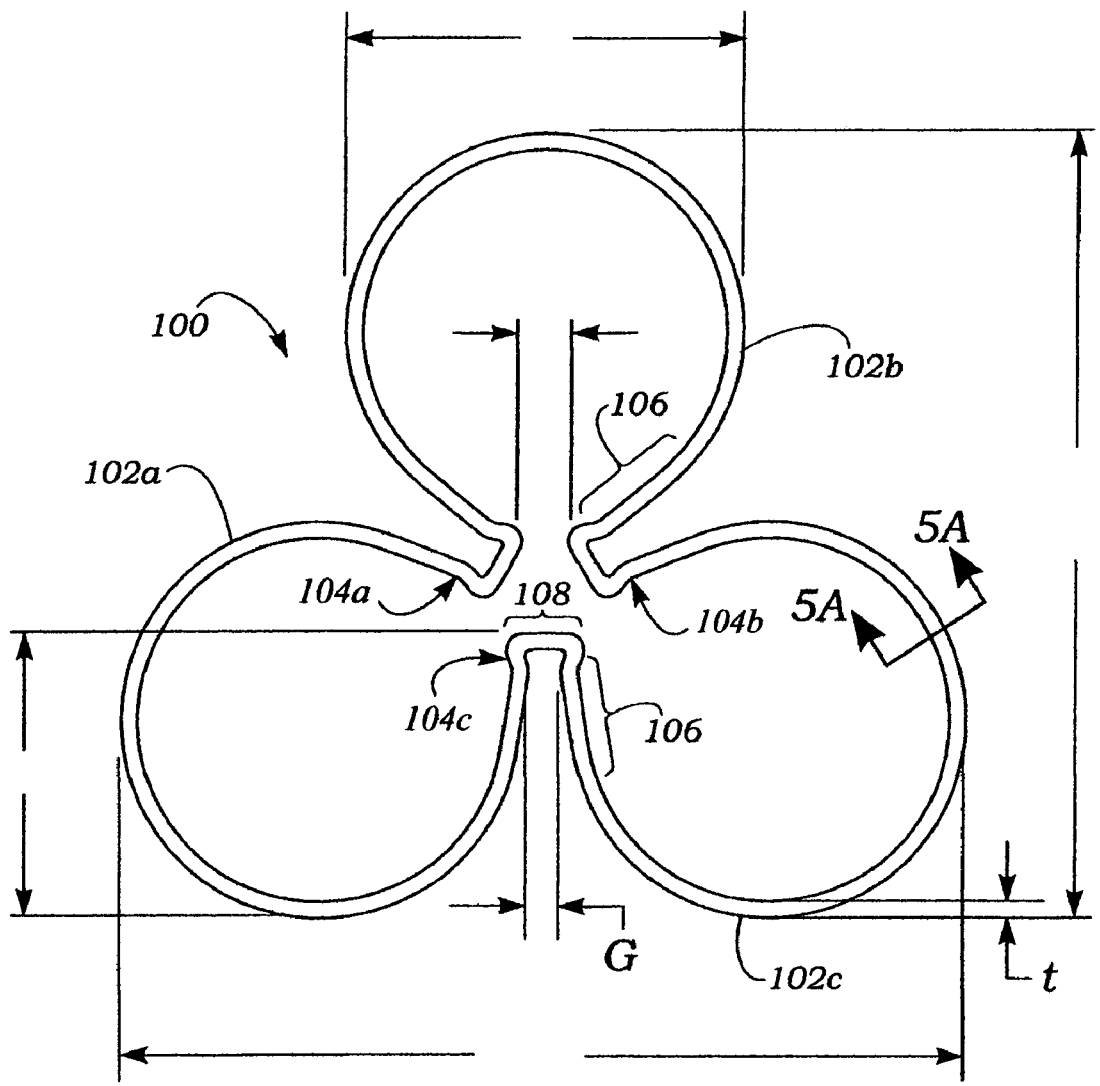
FIG. 5 is a plan view of a two-dimensional heart valve support frame blank of the present invention.

With reference now to FIG. 5, a two-dimensional support frame blank 100 is shown in plan view, illustrating the aforementioned three-leaf clover pattern. As before, there are three generally circular cusps 102a, 102b, 102c separated by three inwardly directed commissures 104a, 104b, and 104c. Each commissure 104 is formed by a pair of generally asymptotic regions 106 projecting from the adjacent cusps 102 and a tip region 108. The asymptotic regions 106 converge until they are separated by a narrow gap G just outward from the tip region 108. The tip region 108 is desirably wider than the gap G, and thus has a greater radius of curvature and is more flexible than the tip would be if the asymptotic regions 106 were simply joined by a round section. The widened tip region 108 helps to prevent the commissures 104 from piercing any fabric covering attached thereover in the assembled valve.

Figure 5A:
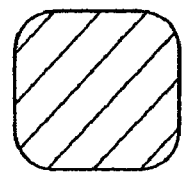
FIG. 5A is a cross-sectional view of the support frame blank of FIG. 5, taken along line 5A-5A.

FIG. 5A illustrates a cross-section through one of the cusps 102 of the support frame blank 100. This embodiment is square with rounded corners, preferably from electropolishing, although other configurations are contemplated. The cross-sectional thickness, given as t in FIG. 5, is desirably relatively slender, preferably between about 0.46-0.76 mm (0.018-0.030 inches). More preferably, the thickness is about 0.66 mm (0.026 inch). If the cross-section is circular (or other shape) the diameter (or effective diameter) would be within the same range.

Methods of Manufacture

Figure 10:
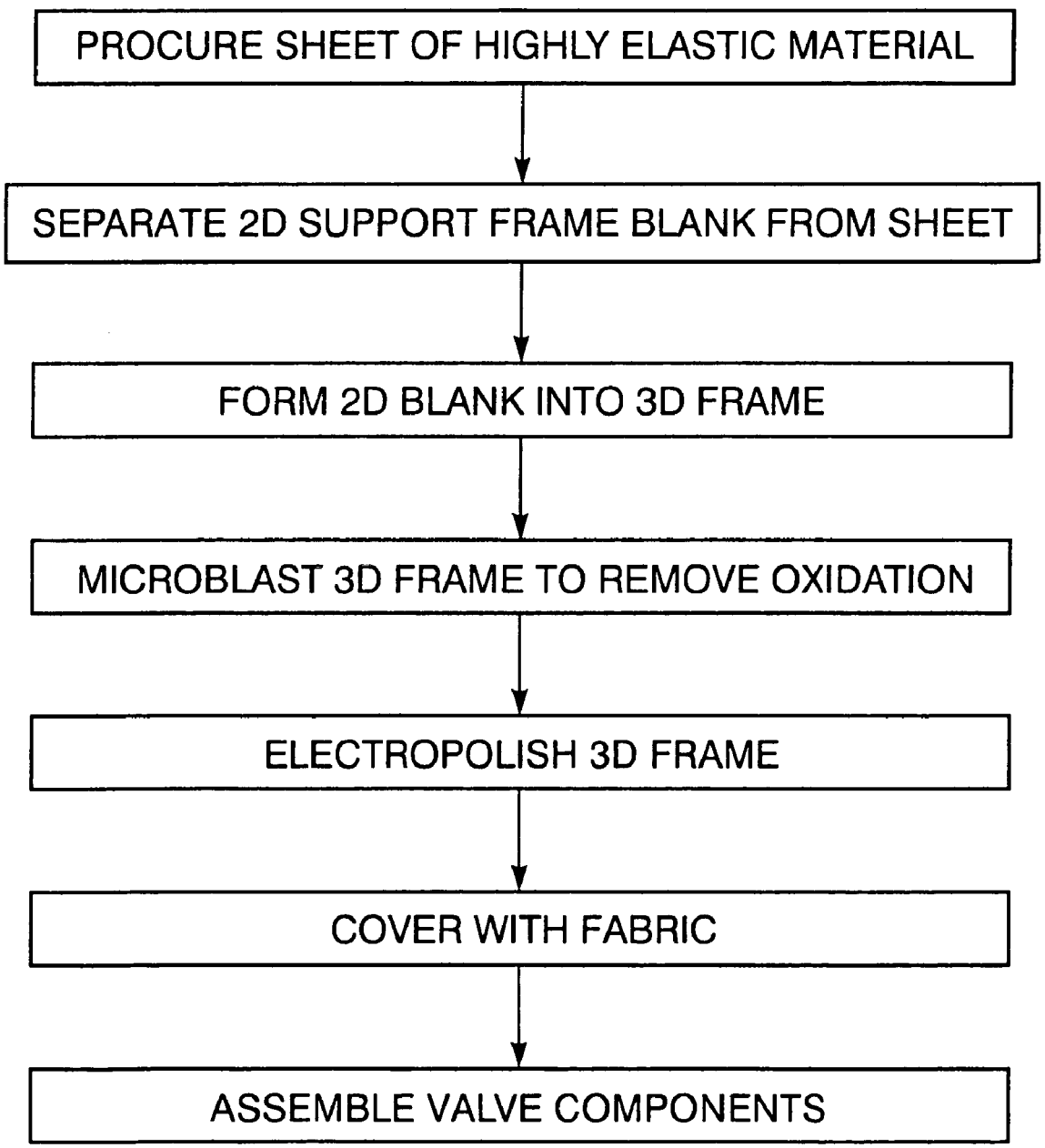
FIG. 10 is a flowchart illustrating an exemplary heart valve support frame manufacturing process.

The following explains a preferred sequence of manufacturing steps to result in the two-dimensional blank 100 of FIG. 5, and then a three-dimensional support frame. This manufacturing sequence is specifically designed for support frame blank 100 made of superelastic material, preferably NITINOL, and can be seen in the flowchart of FIG. 10. A similar process for conventional, merely elastic metals will be also described below. FIG. 10 is an overview of an entire exemplary manufacturing process in flowchart form.

Initially, a flat sheet of elastic material is procured and cleaned. The two-dimensional support frame blank 100 is then separated from the surrounding sheet of material by photo/chemical etching, laser cutting, electric discharge machining, or similar processes. The particular shape of the blank 100 is obtained with knowledge of the end product three-dimensional support frame, as will be described below. At this stage, the cross-section of the blank 100 is either square or rectangular with relatively sharp corners. For the sake of producing uniform stresses when cold working the blank 100, the cross-section is desirably square.

The blank 100 is then forced into approximately the final shape of the heart valve support frame by, for example, fitting it over a mandrel 110 as seen in FIGS. 6 and 7A-7C. The mandrel 110 has an exterior conical body 112 with a rounded nose 114. The mandrel 110 further includes a disk-like base 116, a first set of three pins 118 closely adjacent the base, a second set of three pins 120 positioned farther away from the base, and a set of commissure orientation pins 122 located even farther from the base. These pins can best be seen in cross-section FIG. 7C.

Although not shown, it will be appreciated by the reader that by taking the two-dimensional blank 100 of FIG. 5 and forcing it over the nose 114, the commissures 104 are forced upward and outward, such that the blank assumes the three-dimensional shape 126 seen in FIG. 6. The commissures 104 are registered with the set of commissure orientation pins 122. The superelasticity of the material permits this extreme deformation.

Figure 7C:
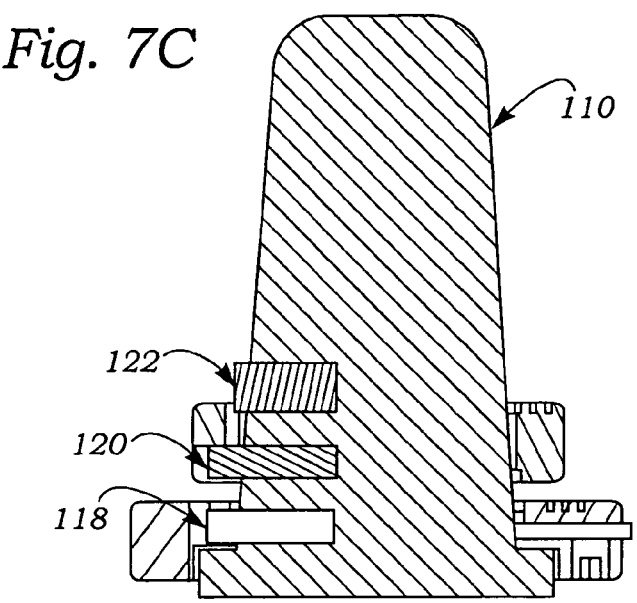
FIG. 7C is a longitudinal cross-sectional view taken through the mandrel apparatus and support frame mounted thereon, and taken along line 7C-7C.
Figure 8B:
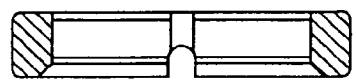
FIGS. 8A and 8B are plan and sectional views, respectively, of a lower ring element of the mandrel apparatus seen in FIGS. 6-7.
Figure 9B:
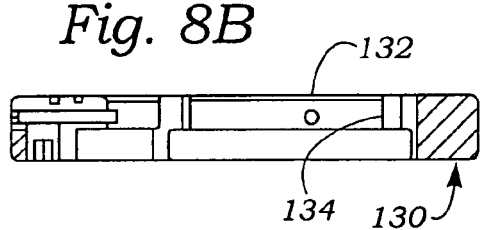
FIGS. 9A and 9B are plan and sectional views, respectively, of an upper ring element of the mandrel apparatus seen in FIGS. 6-7.
Figure 8A:
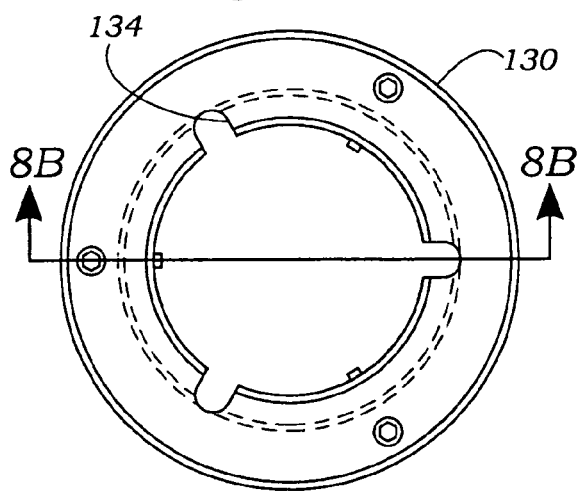
Figure 9A:
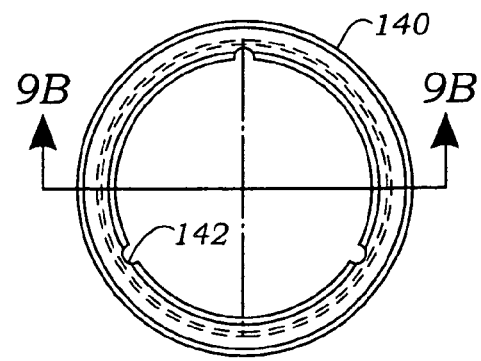

Next, a first ring element 130 (FIGS. 8A and 8B) is lowered over the mandrel 110 until a series of cusp pins 132 contact the base 116. The ring element 130 further includes three cutouts 134 which facilitate passage over the sets of pins 118, 120, and 122, and also orient the ring element. The inner diameter of the ring element 130 is sized slightly larger than the outer diameter of the conical body 112 at its lowest end such that the ring element forces the three-dimensional blank 126 against the exterior of the mandrel body. A second ring element 140 (FIGS. 9A and 9B) more effectively presses the three-dimensional blank 126 against the mandrel body 112. That is, the second ring element 140 passes over the mandrel nose 114 until a series of cutouts 142 register with the commissure orientation pins 122. The final assembly in this manufacturing step is seen in cross section in FIG. 7C. The second ring element 140 descends until it rests on the second series of pins 120, as seen in FIG. 7C, at which point the inner diameter presses the three-dimensional blank 126 against the mandrel body 112. Although two ring elements are shown and described, a single element may also be used.

Once the three-dimensional blank 126 is forced to assume the exterior shape of the mandrel 110 it is set into that shape, preferably by heating. A superelastic alloy such as NITINOL can withstand a relatively large magnitude of strain without deforming, such as when converting the two-dimensional blank 100 into the three-dimensional blank 126, but it will spring back into the original shape unless set to that modified shape. Consequently, heat is applied to the blank 126 when it is maintained over the mandrel 110 resulting in a shape set. The particulars of this operation will not be explained in exhaustive detail other than to say that the particular temperature and time of the shape setting operation depend on the alloy composition, configuration of the workpiece, and history including the degree of cold work already associated with the material. An exemplary embodiment involves a NITINOL alloy having an atomic composition of about 50-50 Nickel (Ni) to Titanium (Ti), which corresponds to between about 55-57% Ni (preferably about 56%) by weight, between about 43-45% Ti (preferably about 54%) by weight, and trace elements such as Carbon and Oxygen. It should be noted that the presence of Oxygen and Carbon should each be limited to less than 500 ppm to help avoid brittleness and ensure an adequate fatigue life of the final support frame. The shape set is done at 560° C.±38° C. (1040° F.±100° F.) for 4.0±2.0 minutes. Even then, once removed from the mandrel assembly, the blank 126 will spring slightly outward and take the form of the final heart valve support frame.

As mentioned above, a different process will be used for more conventional metals such as ELGILOY or titanium. These metals are not superelastic, and thus will not withstand the strains associated with directly converting the two-dimensional form to the three-dimensional form. Therefore, after separating the two-dimensional pattern from the sheet, the final form of the support frame is reached by gradually (i.e., in stages) plastically-deforming the blank. After each deformation step the blank is annealed to remove residual stresses by applying heat for a particular amount of time. The tools used to bend such blanks are not shown in present application, but one of skill in the art will understand that they take form of interpolated shapes between the mandrel 110 and a mandrel with a much shallower conical angle. Although this process is relatively straightforward, the aforementioned single step formation of a superelastic support frame is preferred.

Another way to obtain the final heart valve support frame is to start with a tube of elastic or superelastic material and separate a continuous support frame blank therefrom using the aforementioned means (e.g., laser cutting). The support frame is then modified into a non-tubular shape, so as to describe a conical surface of revolution, for example. The modification of a superelastic material such as NITINOL is accomplished by holding the blank into the desired shape and setting that shape with heat, for example. For a elastic material such as ELGILOY, the blank would be plastically deformed into the desired shape and annealed to remove residual stresses. A mandrel such as described and shown previously could be used to define the conical support frame shape.

FIG. 10 illustrates an exemplary heart valve support frame manufacturing process that involves converting a 2-dimensional blank into a 3-D support frame. After the three-dimensional support frame has been formed into shape it is subjected to surface treatment to round the edges. Mechanical, chemical or electrochemical processes can be used, including tumbling, corner grinding, chemical etching, or microblasting and electropolishing as shown. Sometimes two or more of these processes are used in conjunction with each other to obtain the desired finish. For example, tumbling and electropolishing can be used together to round corners as well as get the desired surface finish. Rounding of the corners of the cross-section minimizes potential sites for stress concentration. The resulting structure is a single piece, continuous heart valve support frame that has rounded corners and a smooth surface.

Figure 11:
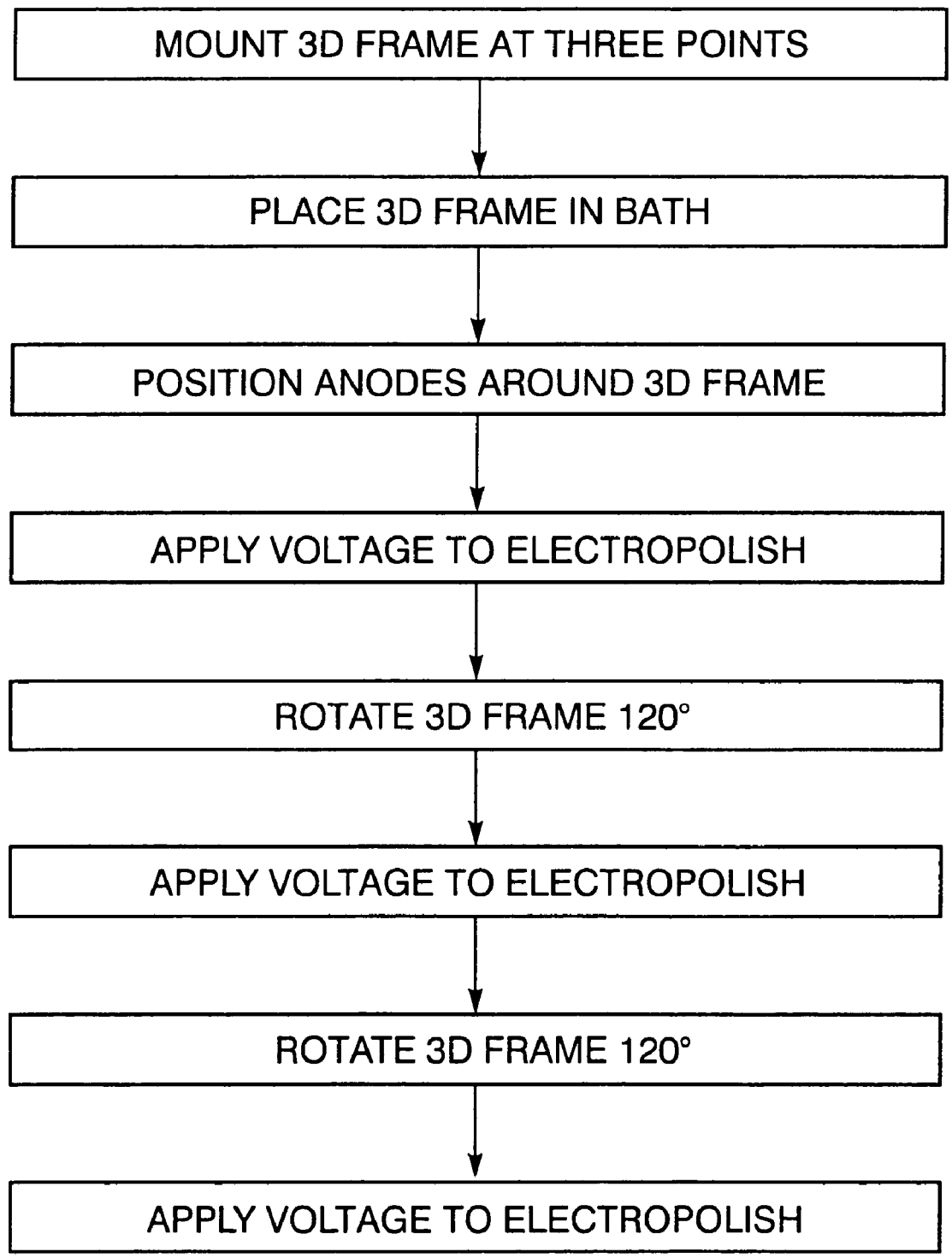
FIG. 11 is a flowchart illustrating an exemplary process for surface treating a heart valve support frame of the present invention.

FIG. 11 is a flowchart describing one particular sequence of events in a surface treating process of the present invention. The goal of the process is to reduce surface defects and roughness to reduce the stresses associated with prolonged use in the body. That is, the support frame is subjected to millions of cycles of systolic-diastolic movement, and its fatigue life is a large concern.

The process begins with the formation of the 3D support frame as described above. To ensure uniform treatment, the frame is mounted or held on a support at three points, preferably along the asymptotic regions 106 as seen in FIG. 5, though other configurations are possible. As mentioned above and seen in FIG. 10, the frame has previously been microblasted to remove oxidation and permit proper conduction to the exterior surface. The frame is submerged in a conductive fluid bath of chemical, for example nitric acid and methanol. In one embodiment, the conductivity of a nitric acid and methanol fluid bath desirably ranges between about 140-190 µs at 23° C. and is monitored periodically to maintain this range. The process desirably occurs at a much lower temperature but this calibration at about room temperature correlates to the proper conductivity at operating temperatures.

There are a number of control variables for the electropolishing process other than the bath conductivity, including the temperature (desirably about −30° C.±2° C.), voltage (desirably between 9-10 V, and more preferably about 9.5 V), current density, agitation of the fluid in the bath, anode and cathode configurations and distance, frame holding arrangement, and others incidental to the process. Desirably the stainless steel bath tank itself provides the cathode and a pair of plates on either side of the frame provide the anodes. However, other arrangements are feasible. It has also been found desirable to rotate the frame three times during the electropolishing to ensure symmetric material removal.

One of the tasks in setting up a manufacturing process as described herein involves carefully calculating the shape of the two-dimensional blank, which will then be bent into the three-dimensional form. One way to perform this calculation involves utilizing a finite element program. Such programs are common in the design industry and generally simulate or model real workpieces and their response to simulated forces and deflections.

To begin, a finite element model of the final configuration of the support frame is input into the program. The frame is modeled with circular cross-section beam elements. Next, vertical displacements are imposed on all the nodes between the beam elements to bring the frame model into a plane. The other degrees of freedom are not constrained to guarantee that the flat pattern will not be carrying any extra load. The model is then updated with the appropriate cross-section, such as square, and the stress in the two-dimensional pattern is canceled. The intent is to reproduce the pattern "as cut" from a sheet of material.

In the finite element program, the two-dimensional pattern is mounted around a simulated mandrel, much as described above. Contact detection is enabled between the frame and mandrel, and displacements are imposed to the cusp nodes. This simulates the frame being pulled down over the mandrel. Mounting of the first ring element is simulated by imposing displacements on the cusp nodes of the frame to bring them in contact with mandrel. The shape of the model is then compared to the shape of the final support frame. At this point, only the cusp and commissure nodes match and a determination is made where the model is farthest way from the mandrel. Once done, placement of a second ring element is simulated at the location where the frame is farthest way from the mandrel. This is normally sufficient to anchor the frame model firmly against the mandrel model.

Finally, a comparison between the frame model and the desired support frame shape is made along the whole frame. If there is a mismatch, the geometry of the initial two-dimensional pattern is adjusted accordingly, and a process is repeated until the correct shape is obtained.

It will be appreciated that the invention has been described hereabove with reference to certain examples or preferred embodiments as shown in the drawings. Various additions, deletions, changes and alterations may be made to the above-described embodiments and examples, and it is intended that all such additions, deletions, changes and alterations be included within the scope of the following claims.

What is claimed is:

1. A method of forming a heart valve support frame, comprising:
   providing a heart valve support frame having an undulating shape with three cusps and three commissures; and
   electropolishing the heart valve support frame by twice rotating the heart valve support frame 120° from an initial position during the electropolishing process to ensure symmetric material removal.

2. The method of claim 1, wherein the heart valve support frame is metallic and has a rectilinear cross-section.

3. The method of claim 1, wherein the heart valve support frame is made of NITINOL.

4. The method of claim 1, further including: prior to electropolshing, first removing oxidation from an outer surface of the heart valve support frame.

5. The method of claim 4, wherein the step of removing oxidation comprises microblasting the outer surface of the heart valve support frame.

6. The method of claim 1, wherein the step of electropolishing comprises:
   submerging the heart valve support frame into a conductive fluid bath;
   providing an anode and a cathode; and
   flowing a current between the anode and the cathode to electropolish the heart valve support frame.

7. The method of claim 6, wherein the step of providing an anode comprises positioning plate anodes within the conductive fluid bath around the heart valve support frame.

8. The method of claim 6, wherein the conductive fluid bath comprises nitric acid and methanol.

9. The method of claim 6, wherein the conductive fluid bath is maintained at a temperature of between about −28 to −32° C.

10. The method of claim 6, wherein the conductive fluid bath is maintained at a conductivity level of between about 140-190 μs at 23° C.

11. The method of claim 6, wherein the current flows at a voltage of between about 9-10 V.

12. The method of claim 1, wherein each commissure is formed by a pair of generally asymptotic regions projecting from the adjacent cusps and a tip region, the method further comprising holding the heart valve support frame at three of the asymptotic regions.

13. A method of forming a heart valve support frame, comprising:
   providing a heart valve support frame having an undulating shape with three cusps separated by three commissures;
   submerging the heart valve support frame into a conductive fluid bath;
   within the conductive fluid bath, holding the heart valve support frame at discrete points around the undulating shape;
   providing an anode and a cathode and flowing a current between the anode and the cathode to electropolish the heart valve support frame within the conductive fluid bath; and
   twice rotating the heart valve support frame 120° from an initial position during the electropolishing process to ensure symmetric material removal.

14. The method of claim 13, wherein the heart valve support frame is made of NITINOL.

15. The method of claim 13, wherein the step of providing an anode comprises positioning plate anodes within the conductive fluid bath around the heart valve support frame.

16. The method of claim 13, further comprising:
   holding the heart valve support frame at just three points around the undulating shape.

17. The method of claim 13, wherein each commissure is formed by a pair of generally asymptotic regions projecting from the adjacent cusps and a tip region, the method further comprising:
   holding the heart valve support frame at three of the asymptotic regions.

* * * * *